United States Patent [19]

Thompson

[11] 4,288,296

[45] Sep. 8, 1981

[54] DECOMPOSITION INHIBITORS FOR HIGH TEMPERATURE STORAGE AND DISTILLATION OF CHLORINATED PHENOLS

[75] Inventor: Leonard R. Thompson, Midland, Mich.

[73] Assignee: The Dow Chemical Company, Midland, Mich.

[21] Appl. No.: 117,733

[22] Filed: Feb. 1, 1980

Related U.S. Application Data

[63] Continuation-in-part of Ser. No. 23,867, Mar. 26, 1979, abandoned.

[51] Int. Cl.³ .................. B01D 3/34; C07C 37/74; C07C 39/36
[52] U.S. Cl. .................................. 203/6; 203/63; 203/91; 568/702; 568/755
[58] Field of Search ............... 203/6, 63, 38, 64, 91, 203/56; 568/702, 755

[56] References Cited

U.S. PATENT DOCUMENTS

| | | | |
|---|---|---|---|
| 3,655,520 | 4/1972 | Harkins | 203/6 |
| 3,816,268 | 6/1974 | Watson et al. | 203/59 |
| 3,852,160 | 12/1974 | Watson et al. | 203/6 |
| 3,852,161 | 12/1974 | Yoshimine et al. | 568/755 |
| 3,909,365 | 10/1975 | Christena | 203/6 |
| 4,016,047 | 4/1977 | Christena | 203/6 |
| 4,142,943 | 3/1979 | Kobel et al. | 203/6 |

OTHER PUBLICATIONS

Biltz et al., Berichte d. Deutsche Chemie Gesellschaft, vol. 37, 4017–4018, (1904).

Primary Examiner—Wilbur L. Bascomb, Jr.
Attorney, Agent, or Firm—Charles J. Enright

[57] ABSTRACT

The decomposition of chlorinated phenols, especially pentachlorophenol, during exposure to high temperatures (e.g., storage and distillation) is markedly reduced by incorporating into the molten chlorinated phenol at least about 0.25 percent by weight of said impure chlorinated phenol of at least one monohydric primary alcohol having at least 14 carbon atoms, one hydroxyl group, and devoid of any other heteroatoms or ether linkages; selected from the group consisting of straight-chain or branched monohydric primary alcohols or a mixture of said straight-chain or branched monohydric primary alcohols.

10 Claims, No Drawings ly chlorinated phenols are not completely stable at elevated temperatures and will tend to decompose during storage or distillation to form large volumes of hydrogen chloride and tar. Product degradation is attributed to the presence of metal ions in storage and process vessels and small amounts of catalyst residue, i.e., aluminum and iron chlorides present in the commerical material. Elevated temperatures accelerate the decomposition reactions. Thus, an economical process for purifying chlorinated phenols which simultaneously allows the removal of undesirable impurities and eliminates the decomposition of the chlorinated phenol at the elevated temperatures required for distillation, would be a highly desirable advance in the art for the production of an environmentally safe, aesthetically acceptable, chlorinated phenol biotoxicant.

SUMMARY OF THE INVENTION

Chlorinated phenols which are essentially free of undesirable impurities and unsatisfactory physical properties are obtained by adding a small amount of inhibitor and distilling the product. The inhibitor is selected from the group consisting of straight-chain or branched primary alcohols, having one hydroxyl group and devoid of any other heteroatoms or ether linkages, and having at least 14 carbon atoms, or a mixture of said straight-chain or branched monohydric primary alcohols. The inhibitor is added to the impure molten chlorinated phenol prior to distillation.

DETAILED DESCRIPTION OF THE INVENTION

Although the process of the present invention may advantageously be performed on any crude chlorinated phenol, it has been found that the present process is particularly applicable to the removal of dark color-forming impurities from pentachlorophenol and the stabilization of pentachlorophenol from decomposition during high temperature storage or distillation.

When crude, dark-colored pentachlorophenol exits the reactor vessel in a molten state at temperatures above its freezing temperature, i.e., 185° C., it begins to decompose into HCl and tar. If crude pentachlorophenol is maintained in the molten state and heated to even higher temperatures required for distillation, significant decomposition occurs. It is advantageous to add a small amount of an inhibitor selected from the group consisting of a straight-chain or branched monohydric primary alcohol having at least 14 carbon atoms, or a mixture of said straight-chain or branched monohydric primary alcohols. The addition of the monohydric primary alcohol significantly retards the accelerated decomposition of impure pentachlorophenol during exposure to high temperatures, e.g., 230° C.–310° C., prior to and during distillation.

A suitable quantity of monohydric primary alcohol is about 0.25 percent to 50 percent, preferably 0.5 to 10 percent by weight of the crude pentachlorophenol. These figures represent practical limits rather than critical amounts. Any significant amount provides some stabilizing effect. Preferably, no more than 10 percent of the primary alcohol is used. Examples of commonly available primary alcohols which are useful in the practice of the present invention include: 1-tetradecanol, 1-pentadecanol, 1-hexadecanol, 1-octadecanol, 1-nonadecanol, 1-eicosanol, 1-heneicosanol, 1-docosanol, 1-tricosanol, 1-tetracosanol, 1-pentacosanol, 1-hexacosanol, 1-heptacosanol, 1-octacosanol, 1-nonacosanol, 1-triacontanol, 1-hentriacontanol, 1-dotriacontanol, 1-tritriacontanol, 1-tetratriacontanol, 1-pentatriacontanol, 1-hexatriacontanol, 1-heptatriacontanol, 1-octatriacontanol, 1-nonatriacontanol, 1-tetracontanol, branched $C_{14}$–$C_{40}$ monohydric primary alcohols and the like.

Primary alcohols having at least 14 carbon atoms, one hydroxyl group and devoid of any other heteroatoms and ether linkages, have a sufficiently high boiling point to facilitate the separation of pentachlorophenol from high boiling impurities. The high boiling impurities remain in the distillation vessel while the impurity-free pentachlorophenol exits the distillation vessel. The preferred $C_{14}$ and higher monohydric primary alcohols continue to exert their stabilizing effect throughout the distillation and eliminate the decomposition of pentachlorophenol at the distillation temperatures. The monohydric primary alcohols having at least 14 carbon atoms may be straight-chain, branched or mixtures thereof. It is also preferred that the monohydric primary alcohol reactant, individually or as a mixture, having a boiling point, at atmospheric pressure, of at least about 310° C.

The addition of the monohydric primary alcohol inhibitor may be by any suitable means; however, it is preferred that the addition be accompanied by agitation, stirring or mixing so that a uniform mixture of the alcohol and impure pentachlorophenol results.

Conventional vacuum distillation equipment is satisfactory to carry out the distillation. For example, the distillation apparatus may be a vacuum batch still with heat being supplied to the still by a forced circulation reboiler heated with circulating hot oil. Vapors which may be passed out the top of the batch pot through a column containing a small amount of packing material may be condensed in a shell and tube-type condenser (vapor on the inside of the tubes and high pressure steam generated on the outside). A reduced pressure is maintained on the system as, for example, by dual stage jet ejector in a manner well-known in the art.

Typically, the distillation is performed under vacuum conditions, e.g., at a pressure of about 20 mm up to less than 760 mm Hg, preferably from about 40 mm to about 100 mm Hg and at a temperature of from about 185° C. to 310° C., preferably from about 205° C. to 240° C. Distillate recovery based on the amount of pentachlorophenol distilled versus the amount in the crude feed yields 85–97 percent recovery. If the recovery is based on the amount of pentachlorophenol distilled versus the total crude feed (including tar), recovery is usually between 75–90 percent depending on the amount of tar in the feed. The early addition of a suitable amount of inhibitor (i.e., $C_{14}$ and higher monohydric primary alcohols) will decrease the amount of tar in the feed, which, as noted earlier, begins to decompose prior to distillation.

When the distillation is carried out under the conditions noted above, the liquid distillate is water-white in color, when solidified it is an off-white unless it comes in contact with iron. The contact with iron, while molten, causes it to darken; the degree of darkness depends on the length of time it is in contact with the iron.

The following examples illustrate the invention but are not to be taken as limiting its scope. In the examples, quantities of material are expressed in terms of parts by weight, unless otherwise specified.

EXAMPLE 1

(Measurement of Decomposition During High Temperature Storage)

A 500 ml flask equipped with a thermometer, heat lamp and controller, 1"×1' glass tube condenser connected to a trap containing 100 cc of 1 N sodium hydroxide is prepared to simulate storage conditions. To such prepared flask is added 266.4 parts of crude pentachlorophenol, containing residue from a Friedel-Crafts catalyst such as aluminum chloride, and 2.7 parts of 1-hexadecanol, an inhibitor. The mixture is heated and maintained at 230° C. for six hours. During this 6-hour interval, nitrogen is slowly swept across the surface and bubbled into the sodium hydroxide trap. One milliliter samples are withdrawn from the trap and titrated for HCl, one of the major decomposition products of pentachlorophenol. The titration is accomplished with 0.1 N silver nitrate to give percent decomposition. In the table below the results of this experiment are compared with a control sample heated at 230° C. for six hours, under similar conditions, without an inhibitor.

TABLE I

| Crude Pentachlorophenol Decomposition on Storage 6 hours at 230° C. | |
|---|---|
| Inhibitor | % Decomposition |
| none | 15.0 |
| 1-hexadecanol (cetyl alcohol) | 1.8 |

EXAMPLE 2

In a manner similar to that described in Example 1, decomposition during high temperature storage was tested using 266.4 parts of crude pentachlorophenol containing residue from a Friedal-Crafts catalyst and 0.54 parts of 40 mesh iron filings, a metal common in storage equipment and also known to accelerate the decomposition of crude pentachlorophenol. The addition of 2.7 parts of 1-hexadecanol, an inhibitor resulted in pentachlorophenol which decomposed only 1.4 percent after being heated for 6 hours at 230° C.

EXAMPLES 3–5

(Stabilization of Pentachlorophenol to Distillation)

A 500 ml distillation flask is prepared containing 0.54 parts of protruded nickel packing, a steel coupon ⅛"-×½"×2" and having attached a 1"×5" column packed with 19.5 parts of cannon perforated nickel packing and 0.7 parts of mild steel drill turnings. The column and rundown line are heated and insulated to prevent freezing. To the prepared flask is added 266.4 parts of crude pentachlorophenol, containing the residue of a Friedel-Crafts catalyst such as aluminum chloride, and 1 weight percent or 2.7 parts of an inhibitor listed in Table II below. The contents of the flask are heated and distilled at 260° C. under 75 mm Hg pressure through the 1"×5" packed column. The decomposition of the pentachlorophenol was measured by scrubbing the exit gas from the vacuum pump into a trap containing 100 cc of 1 N sodium hydroxide. One milliliter samples are withdrawn from the trap and titrated for HCl content with 0.1 N silver nitrate to show percent decomposition. The results are set forth in Table II below. The percentage yield of purified pentachlorophenol is based on the amount of pentachlorophenol distillate recovered divided by the total crude feed (including tar) multiplied by 100.

TABLE II

| | Crude Pentachlorophenol Distillation 260° C. | | |
|---|---|---|---|
| Example No. | Inhibitor | % Yield of Purified Pentachlorophenol | % Decomposition |
| * | Polyethylene glycol (M.W. 200) | 81.0 | 0.71 |
| 3 | **ALFOL 1618 | 81.3 | 0.10 |
| 4 | ***ALFOL 20+ | 80.2 | 0.20 |
| 5 | 1-Hexadecanol (cetyl | 81.2 | 0.37 |

TABLE II-continued

| Example No. | Inhibitor | Crude Pentachlorophenol Distillation 260° C. % Yield of Purified Pentachlorophenol | % Decomposition |
|---|---|---|---|
| | | alcohol) | |

*Not a part of this invention, for comparison only.
**ALFOL 1618 is a blend of synthetic linear primary alcohols having even-numbered carbon chains in the $C_{14}$-$C_{20}$ range. Manufactured by Conoco Chemicals Division, Continental Oil Company, Houston, Texas.
***ALFOL 20+ is a mixture containing high molecular weight linear primary alcohols in the $C_{20}$-$C_{28}$ range. Manufactured by Conoco Chemicals Division, Continental Oil Company, Houston, Texas.

EXAMPLES 6–7

Each example is performed in a similar manner as Examples 3–5 except that the amount of inhibitor is increased from one percent (2.7 parts) to five percent (13.4 parts) based on the amount of crude pentachlorophenol to be distilled. The results are shown in Table III.

TABLE III

| Example No. | Inhibitor | Crude Pentachlorophenol Distillation with 5% Inhibitor - 260° C. % Yield of Purified Pentachlorophenol | % Decomposition |
|---|---|---|---|
| 6 | *ALFOL 20+ | 83.0 | <0.05 |
| 7 | **EPAL 20+ | 84.6 | 0.05 |

*ALFOL 20+ is a mixture containing high molecular weight linear primary alcohols in the $C_{20}$-$C_{28}$ range. Manufactured by Conoco Chemicals Division, Continental Oil Company, Houston, Texas.
**EPAL 20+ is a blend of linear and branched primary alcohols with carbon numbers from $C_{20}$-$C_{32}$. Manufactured by Ethyl Corporation, Industrial Chemicals Division, Baton Rouge, Louisiana.

What is claimed is:

1. A process for inhibiting the decomposition of chlorinated phenol during exposure to high temperatures, which comprises adding at least 0.25 percent by weight of said chlorinated phenol of at least one primary alcohol having at least 14 carbon atoms, one hydroxyl group, and devoid of any other heteroatoms and ether linkages, selected from the group consisting of straight-chain or branched monohydric primary alcohols and mixtures of said straight-chain or branched monohydric primary alcohols.

2. The process of claim 1 wherein exposure to high temperatures includes storage of molten chlorinated phenol and distillation.

3. The process of claim 1 wherein the chlorinated phenol is crude chlorinated phenol.

4. The process of claim 3 wherein about 0.25 to about 10 percent by weight of inhibitor based on crude chlorinated phenol is present.

5. The process of claim 1 wherein the chlorinated phenol is pentachlorophenol.

6. A process for purifying impure chlorinated phenol which comprises distilling said chlorinated phenol at subatmospheric pressures in the presence of at least about 0.25 percent by weight of said impure chlorinated phenol of at least one primary alcohol having at least 14 carbon atoms, one hydroxyl group, and devoid of any other heteroatoms and ether linkages, selected from the group consisting of straight-chain monohydric primary alcohols, branched monohydric primary alcohols and mixtures thereof, thereby separating said chlorinated phenol from higher boiling impurities.

7. The process of claim 6 wherein about 0.25 to about 10 percent by weight of a monohydric primary alcohol or mixture thereof is present in the distillation mixture.

8. The process of claim 6 wherein the chlorinated phenol is pentachlorophenol.

9. The process of claim 8 wherein the monohydric primary alcohol or mixture thereof has a boiling point, at atmospheric pressure, of at least about 310° C.

10. The process of claim 8 wherein the distillation pressure is below about 100 mm Hg absolute.

* * * * *